United States Patent [19]

Schmid et al.

[11] Patent Number: 5,058,572
[45] Date of Patent: Oct. 22, 1991

[54] ADJUSTABLE CERVICAL COLLAR

[75] Inventors: K. Stephen Schmid, New Vienna, Ohio; Richard A. Brault, Toronto, Canada

[73] Assignee: Ferno-Washington, Inc., Wilmington, Ohio

[21] Appl. No.: 143,362

[22] Filed: Jan. 12, 1988

[51] Int. Cl.⁵ ............................................. A61H 1/02
[52] U.S. Cl. ....................................... 128/75; 128/78; 128/DIG. 23
[58] Field of Search .......... 128/75, 78, 87 B, DIG. 23

[56] References Cited

U.S. PATENT DOCUMENTS

| 4,413,69 | 11/1983 | Garth | 128/76 R |
|---|---|---|---|
| 2,389,690 | 10/1943 | Schreiber | 128/DIG. 23 |
| 4,640,269 | 2/1987 | Goins | 128/78 |
| 4,677,969 | 7/1987 | Calabrese | 128/DIG. 23 |
| 4,708,129 | 11/1987 | Pujals, Jr. | 128/DIG. 23 |
| 4,712,540 | 12/1987 | Tucker et al. | 128/76 R |

OTHER PUBLICATIONS

"Appliances For the Spine and Trunk", Orthopaedic Appliances Atlas, 1952.

*Primary Examiner*—Edgar S. Burr
*Assistant Examiner*—Aaron J. Lewis
*Attorney, Agent, or Firm*—Frost & Jacobs

[57] ABSTRACT

A cervical collar composed essentially of an anterior section and a posterior section interconnected by an elongated strap, with the rear surfaces of the sections covered by cushioning material, the parts preferably being formed from high density polyethylene sheeting with polyethylene foam cushioning material, the parts being interconnected by plastic fasteners. Preferably the sections will be adjustable relative to each other, with one of the sections slidably mounted relative to the other. The configuration of the sections is designed to provided optimum support to achieve immobilization of the cervical spine.

19 Claims, 2 Drawing Sheets

ADJUSTABLE CERVICAL COLLAR

This invention relates to cervical collars, and has to do more particularly with an adjustable cervical collar particularly suited for use in pre-hospital care applications.

BACKGROUND OF THE INVENTION

Numerous types of cervical collars have hitherto been proposed for treating neck injuries which result in muscular strain or nerve pressure in the cervical area. Extrication collars have become extremely important in field rescue operations to immobilize and maintain the cervical spine in a neutral position until a suspected injury can be diagnosed and treated. While surgical collars are presently available which are intended for field rescue use, such devices have left much to be desired with regard to their ease of application as well as their ability to meet other criteria which have been found desirable in a device intended for field use. The present invention overcomes these difficulties by providing a cervical collar specifically designed for rescue uses which not only provides the structural relationships necessary to achieve immobilization of the cervical spine but also provides a structure which may be readily adjusted to accommodate persons of different sizes.

SUMMARY OF THE INVENTION

In accordance with the present invention, the collar is of one-piece design, being composed of a series of interconnected high density polyethylene parts covered in all critical anatomy contacting areas with polyethylene foam, the parts being joined together by plastic rivets.

The collar comprises essentially an anterior section and a posterior section interconnected by an elongated strap which is fixedly secured at one end to the anterior section, this strap being slidably received by the posterior section to permit lateral displacement of the sections relative to each other, thereby permitting ready adjustment of the anterior and posterior sections relative to each other and to the anatomy of the wearer.

A Velcro fastening system is provided to facilitate rapid application of the collar, as well as provide for easy removal.

The all plastic construction makes the collar easy to clean, and also makes it compatible with MRI, CT, and X-ray machines, as well as providing a collar which is useable over a wide temperature range.

In addition to its utility in the field, the collar of the present invention provides a thin side profile which allows it to be easily slipped behind the wearer's neck and also permits the collars to be readily stored in an emergency vehicle either in flat condition or folded to fit into a small storage compartment. Being adjustable to accommodate a number of sizes eliminates the necessity for carrying an assortment of collars of different sizes and hence further reduces the storage space requirements in the rescue vehicle.

A collar constructed in accordance with the present invention is simple and inexpensive to manufacture in that it comprises a series of die-cut parts which are readily assembled utilizing plastic rivets and hence there are minimum tooling requirements.

DESCRIPTION OF THE PREFERRED EMBODIMENT

Figure 1:
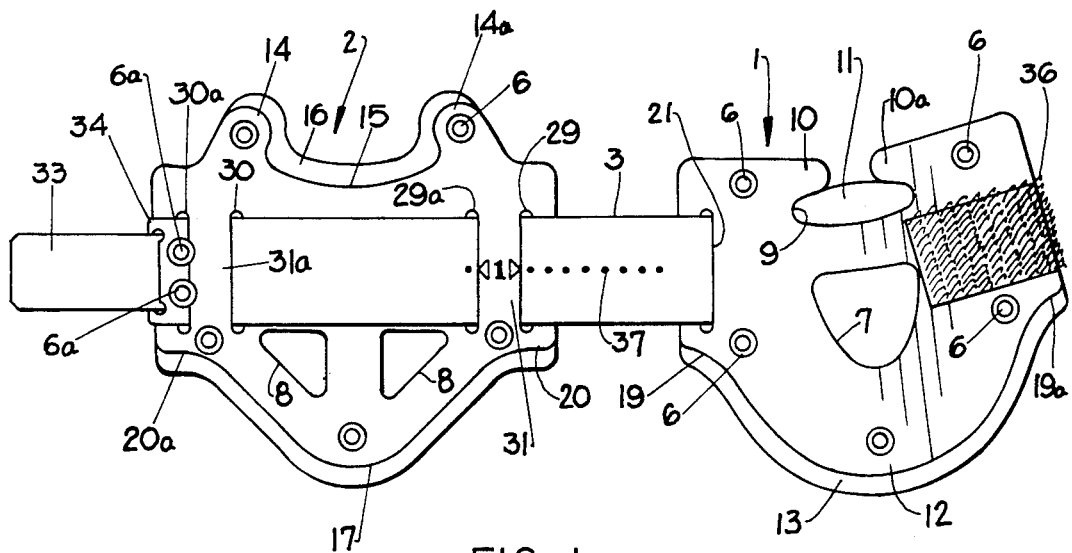
FIG. 1 is a front elevational view of an adjustable cervical collar in accordance with the invention.

Referring first to FIG. 1 of the drawings, a cervical collar in accordance with the invention comprises an anterior section, indicated generally at 1, a posterior section, indicated generally at 2, the two sections being interconnected by an elongated strap 3. All three of these parts are preferably formed from sheets of 1/16" high density polyethylene which is relatively stiff yet flexible.

Figure 2:
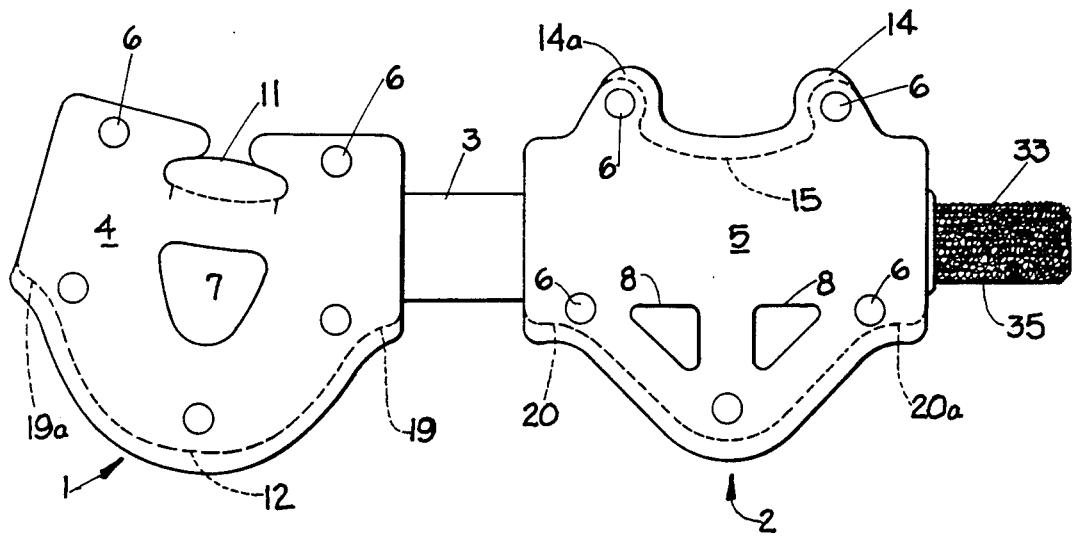
FIG. 2 is a rear elevational view thereof.

As best seen in FIG. 2, the sections 1 and 2 are covered on their rear surfaces with areas of cushioning material 4 and 5, respectively, the cushioning material being attached to the sections by means of plastic rivets 6. Preferably the cushioning material will be formed from pieces of 3/16"-¼" close-celled polyethylene foam which is die-cut to conform to the configuration of the sections 1 and 2, including the throat exposing cut-out 7 in the anterior section and the ventilation cut-outs 8 in the posterior section. The anterior section 1 is also provided with a chin receiving cut-out 9 which also defines an opposing pair of mandible supports 10, 10a designed to control flexion, extension and rotation of the lower jaw. Since the lower jaw will rest on the chin receiving cut-out 9, the cushioning material 4 is provided with an integral seat 11 adopted to fold outwardly over the lower edge of the cut-out 9 to provide padding along the edge of the cut-out 9 which contacts the wearer's lower jaw.

The lowermost edge of the anterior section 1 is of outwardly curved configuration, indicated at 12, which provides for bracing between the underside of the mandible and the sternum. Preferably, the lowermost edge of the cushioning material 4 is extended downwardly beyond the curved edge 12, as indicated at 13, again for the purpose of providing padding along an edge of the collar which contacts the wearer's body.

The posterior section 2 of the collar is configured to provide an integral opposing pair of extensions 14, 14a which coact to provide right and left lateral support for the occipital support 15 extending along the upper edge of the posterior section 2 between the extension 14, 14a. Preferably, the cushioning material 5 will extend upwardly beyond the occipital support 15 and the extensions 14, 14a in the areas where the uppermost portions of the posterior section contact the wearer's head, such extended areas being indicated at 16.

The lowermost edge of the posterior section 2 is also of outwardly curved configuration, indicated at 17, to provide posterior thoracic spine support which, together with the occipital support, act to control extension. The cushioning 5 also extends downwardly beyond the curved edge 17, as indicated at 18, to provide padding where the posterior section of the collar contacts the wearer's body.

It also will be noted that the outermost ends of the curved lowermost edge 12 of the anterior section 1 terminates at its opposite ends in reversely curved areas 19, 19a which find counterparts 20, 20a at the outermost ends of the curved lowermost edge 17 of posterior section 2. The areas 19, 20 and 19a, 20a coact to provide right and left trapezius support which act to control lateral flexion.

Figure 3:
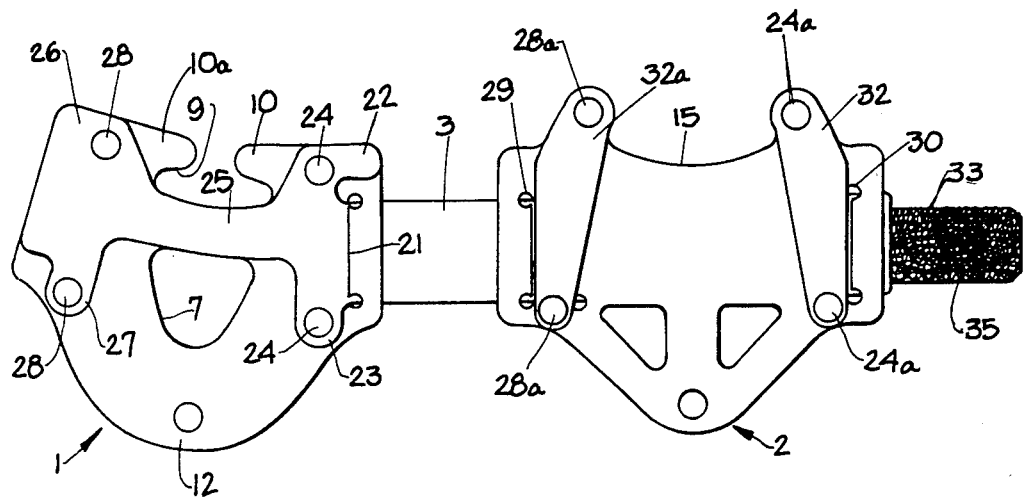
FIG. 3 is a rear elevational view similar to FIG. 2 but with the foam padding removed to illustrate the underlying construction of the parts.

As previously indicated, the anterior and posterior sections of the collar are adjustably interconnected by means of the elongated strap 3 which, as best seen in FIG. 3, extends through a slot 21 in the anterior section 1, the strap having an opposing pair of ears 22 and 23 projecting laterally from the strap 3, the ears each having an opening 24 therein adapted to receive one of the plastic rivets 6 to thereby fixedly secure the strap 3 to the anterior section 1. The strap 3 also has an extension 25 of a size to lie between the chin receiving cut-out 9 and the underlying throat exposing cut-out 7, the strap terminating at its end in oppositely directed enlargements 26, 27 having openings 28 adapted to receive corresponding plastic rivets 6. The ears 22, 23, the extension 25, and the enlargements 26, 27 thus serve to reinforce and strengthen the anterior section 1 and serve as a means to securely fasten the strap 3 to the anterior section 1.

The opposite end of the strap 3 extends through pairs of spaced apart slots 29, 29a and 30, 30a formed in the opposite sides of posterior section 2, the pairs of slots defining webs 31 and 31a therebetween which act to slidably mount the posterior section 2 relative to the strap 3. On its rear surface the posterior section 2 mounts a pair of vertically extending braces 32 and 32a which serve to reinforce the posterior section in the areas of the extensions 14,14a and the webs 31 and 31a, the strap 3 slidably passing between the braces and the rear surface of the posterior section. As is the case of the ears 22,23 and the enlargements 26,27, the braces are provided with rivet receiving openings 24a and 28a which are adapted to receive the correspondingly positioned plastic rivets 6 which interconnect the parts. Preferably the braces 32 and 32a will be formed from the same material as the sections and strap.

Adjacent its distal end the strap 3 is provided with a pair of plastic rivets 6a which serve as stops to establish the fully extended position of the posterior section 2 relative to the anterior section 1, the rivets 6a additionally serving to anchor an attachment tongue 33 the inner end of which extends through a slot 34 immediately adjacent the distal end of strap 3, the tongue 33 preferably comprising a strip of flexible material having a Velcro "eye" 35 (seen in FIG. 2) on its rear surface, the tongue being engageable with an adhesively backed Velcro "hook" 36 adhesively secured to the outer surface of anterior section 1, as seen in FIG. 1.

Figure 4:
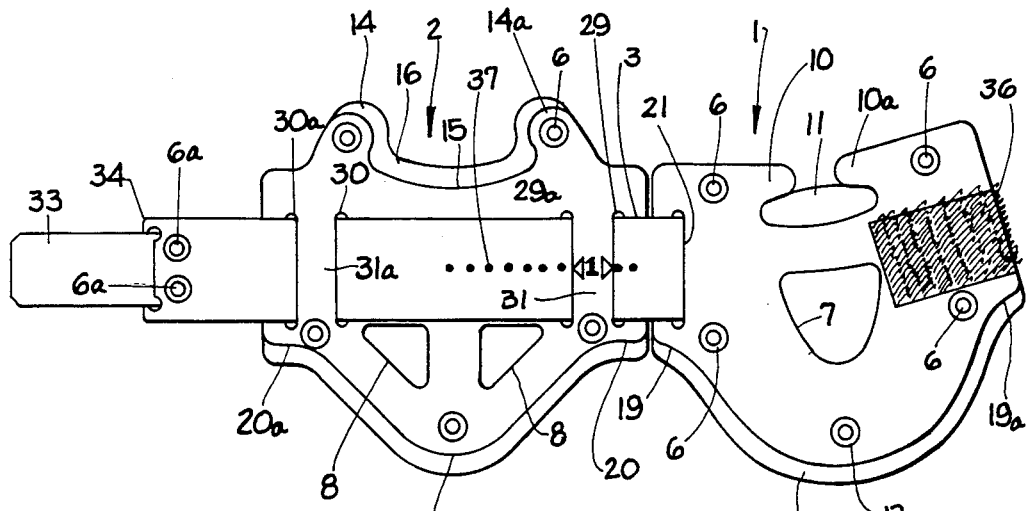
FIG. 4 is a front elevational view similar to FIG. 1 illustrating the collar in an adjusted position of use.

In applying the collar to an injured person and depending upon the person's size, the anterior and posterior sections are adjusted relative to each other by sliding the posterior section 2 along the strap 3 relative to the anterior section 1. To this end, printed indicia in the form of a series of dots or similar calibrations are provided on the outer surface of the strap 3 at equally spaced part intervals, such as ⅛", by means of which rescue personnel may be guided in adjusting the distance between the anterior and posterior sections of the collar in accordance with the size of the wearer. To this end, the web 31 may be of a predetermined width, such as 1", to further identify for rescue personnel the relative positions of the anterior and posterior sections as they encircle the wearer's neck, the sections of the collar being moveable from the fully extended position illustrated in FIG. 1 to the fully contracted position illustrated in FIG. 4, which may be on the order of 3" between the fully retracted and fully extended positions. With this arrangement, the collar may be readily fitted to persons of different sizes with the assurance that all of the desired contact points will be properly positioned and utilized to immobilize the spine with control over extension, flexion, including lateral flexion, and also rotation.

Modifications may be made in the invention without departing from its spirit and purpose. While a preference is expressed for a collar in which the anterior and posterior sections are adjustable relative to each other, the basic configuration of the sections could be utilized in non-adjustable collars, in which event the strap could be fixedly secured to both sections.

What is claimed is:

1. An adjustable essentially planar cervical collar of unitary construction consisting essentially of an anterior section and a posterior section interconnected by an elongated strap extending between and slidably interconnecting said sections, said sections and said strap each being flat and essentially rigid, but sufficiently flexible so that, in use, they may be conformed to the contours of the wearer's head, neck and shoulders, attachment means slidably connecting said strap to one of said sections with one end of said strap projecting freely outwardly beyond said last named section, stop means on said strap to prevent its detachment from the section to which it is slidably connected, fastener means fixedly connecting the opposite end of said strap to the other of said sections, whereby to adjust the position of the sections relative to each other and to the anatomy of the wearer, and securement means on the free end of said strap for securing said collar around the neck of the wearer.

2. The cervical collar claimed in claim 1 wherein the attachment means slidably connected to said strap to one of said sections comprise pairs of spaced apart slots in said last named section defining webs in said section beneath which said strap extends, and wherein the stop means on said strap is positioned to engage one of said webs to establish the fully extended position of said last named section relative to said strap and to the other of said sections.

3. The cervical collar claimed in claim 1 wherein the rear surface of each of said sections is covered with a cushioning material, and wherein fastener means serve to secure said cushioning material to the rear surfaces of said sections.

4. The cervical collar claimed in claim 3 wherein said sections and said strap are formed from high density polyethylene sheeting, wherein said cushioning material is formed from polyethylene foam, and wherein said fastener means comprise plastic rivets.

5. The cervical collar claimed in claim 4 wherein the means on said strap for securing said collar around the neck of the wearer comprises a Velcro fastener.

6. The cervical collar claimed in claim 3 wherein said anterior section is configured to provide a centrally disposed chin receiving opening extending downward from its upper edge, and wherein said cushioning material includes an integral seat in the area of said chin receiving opening adapted to be folded outwardly over the lowermost edge of said opening.

7. The cervical collar claimed in claim 6 including an opposing pair of mandible supports extending inwardly from the opposite sides of said chin receiving opening.

8. The cervical collar claimed in claim 7 wherein the lowermost edge of said anterior section downwardly curved configuration, and wherein said cushioning material projects downwardly beyond said lowermost edge.

9. The cervical collar claimed in claim 3 wherein said posterior section is configured to provide a centrally disposed occipital support on its uppermost edge, said occipital support terminating at its opposite ends in a pair of upwardly projecting extensions, and wherein said cushioning material extends upwardly beyond said occipital support and said extensions.

10. The cervical collar claimed in claim 9 wherein the lowermost edge of said posterior section is of downwardly curved configuration, and wherein said cushioning material extends downwardly beyond said lowermost edge.

11. The cervical collar claimed in claim 1 wherein said strap is secured to the other of said sections by means of a slot in said last named section through which said strap passes, and a pair of laterally projecting ears on said strap lying immediately beyond said slot.

12. The cervical collar claimed in claim 11 wherein the other of said sections comprises the anterior section and has a centrally disposed chin receiving cut-out extending downwardly from its upper edge, wherein said strap includes an extension the upper edge of which coincides with the lowermost edge of said cut-out, and wherein said extension terminates in upper and lower enlargements lying beyond said cut-out, said strap being secured to said anterior section by means of fasteners connecting said ears and said enlargements to said anterior section.

13. The cervical collar claimed in claim 2, wherein said strap is slidably connected to said posterior section, and wherein said posterior section has a spaced apart pair of braces secured to its rear surface in the areas of said webs, said strap extending between said braces and the rear surface of said posterior section.

14. An essentially planar cervical collar of unitary construction for effectively immobilizing and maintaining the cervical spine in a neutral position, said collar comprising essentially an anterior section and a posterior section interconnected by a strap, said sections and said strap each being flat and essentially rigid but sufficiently flexible so that, in use, the collar may be conformed to the contour of the wearer's head, neck and shoulders, said anterior section having a centrally disposed chin receiving cut-out extending downwardly from its uppermost edge, including an opposing pair of mandible supports projecting inwardly from the opposite sides of said chin receiving cut-out, the lowermost edge of said anterior section being of downwardly curved configuration to provide bracing between the underside of the mandible and the sternum, said posterior section being configured along its upper edge to provide a centrally disposed occipital support for the base of the occipit, said occipital support being subtended by an opposing pair of upwardly projecting temporal supporting extensions which provide lateral support for the occipit, the lowermost edge of said posterior section being of downwardly curved configuration to provide posterior thoracic spine support, and securement means for securing said collar around the neck of the wearer, whereby to effectively immobilize and maintain the wearer's cervical spine in a neutral position.

15. The cervical collar claimed in claim 14 including cushioning material secured to the inner surface of said anterior section, an integral seat formed in said cushioning material in the area of said cut-out, said seat being adapted to be folded outwardly over the lower edge of said cut-out, cushioning material secured to the inner surface of said posterior section, said cushioning material projecting upwardly beyond said occipital support and said extensions, and wherein said cushioning material projects downwardly beyond the curved lower edges of said sections.

16. The cervical collar claimed in claim 14 including means fixedly securing one end of said strap to said anterior section, and means slidably connecting said posterior section to the opposite end of said strap, including stop means associated with said strap to prevent detachment of said posterior section from said strap.

17. The cervical collar claimed in claim 16 wherein the means fixedly securing one end of said strap to said anterior section includes a slot in said anterior section through which said strap passes, laterally extending ears on said strap immediately beyond said slot, and fastener means securing said ears to said anterior section.

18. The cervical collar claimed in claim 16 wherein the means slidably connecting said posterior section to said strap comprises pairs of web defining slots in said posterior section through which said strap extends, and wherein said stop means associated with said strap to prevent detachment of said posterior section comprises web engaging rivets.

19. The cervical collar claimed in claim 18 including reinforcing braces secured to the rear surface of said posterior section, said braces underlying said webs and said upwardly projecting extensions and being fastened to said posterior section so as to permit said strap to slide between said braces and the rear surface of said posterior section.

* * * * *

UNITED STATES PATENT AND TRADEMARK OFFICE
CERTIFICATE OF CORRECTION

PATENT NO. : 5,058,572

DATED : October 22, 1991

INVENTOR(S) : K. Stephen Schmid and Richard A. Brault

It is certified that error appears in the above-identified patent and that said Letters Patent is hereby corrected as shown below:

Column 4 - Claim 2 - Line 39 - "connected to" should be deleted and replaced with --connecting--.

Column 4 - Claim 2 - Line 40 - "comprise pairs" should be deleted and replaced with --comprises pairs--.

Column 5 - Claim 8 - Line 5 --is of-- should be inserted after "section".

Signed and Sealed this

Second Day of March, 1993

Attest:

STEPHEN G. KUNIN

*Attesting Officer*  *Acting Commissioner of Patents and Trademarks*